(12) United States Patent
Umakoshi et al.

(10) Patent No.: US 7,973,167 B2
(45) Date of Patent: Jul. 5, 2011

(54) METAL COMPLEX, LIGHT-EMITTING DEVICE AND DISPLAY

(75) Inventors: Keisuke Umakoshi, Nagasaki (JP); Keizo Saito, Nagasaki (JP); Masayoshi Onishi, Nagasaki (JP); Shoji Ishizaka, Sapporo (JP); Noboru Kitamura, Sapporo (JP)

(73) Assignee: Nagasaki University, Nagasaki-Shi, Nagasaki (JP)

( * ) Notice: Subject to any disclaimer, the term of this patent is extended or adjusted under 35 U.S.C. 154(b) by 0 days.

(21) Appl. No.: 12/529,742

(22) PCT Filed: Mar. 5, 2008

(86) PCT No.: PCT/JP2008/053957
§ 371 (c)(1),
(2), (4) Date: Oct. 16, 2009

(87) PCT Pub. No.: WO2008/108407
PCT Pub. Date: Sep. 12, 2008

(65) Prior Publication Data
US 2010/0105918 A1    Apr. 29, 2010

(30) Foreign Application Priority Data
Mar. 6, 2007    (JP) ................. 2007-056128

(51) Int. Cl.
*C07F 15/00* (2006.01)
(52) U.S. Cl. ..................................... 548/101
(58) Field of Classification Search .......... None
See application file for complete search history.

(56) References Cited

U.S. PATENT DOCUMENTS
2009/0198069 A1    8/2009  Umakoshi et al.
2010/0010231 A1*   1/2010  Umakoshi et al. ........... 548/101

FOREIGN PATENT DOCUMENTS
JP      2008-081401 A    4/2008
WO  WO 2006/101276 A1    9/2006

OTHER PUBLICATIONS

International Search Report (PCT/ISA/210) for PCT/JP2008/053957 mailed May 20, 2008.
K. Saito et al., "3,5-Dimethylpyrazole o Haiishi to shita Kakkin—11-zoku Kinzoku Kongo Sakutai no Gosei to Seishitsu", Dai 87 Annual Meeting on Chemical Society of Japan in Spring (2007) Koen Yokoshu I, issued on Mar. 12, 2007, p. 541, '2 R2-07'.
M. Baldo et al., "Very High-Efficiency Green Organic Light-Emitting Devices Based on Electrophosphorescence", Applied Physics Letters, Jul. 5, 1999, pp. 4-6, vol. 75, No. 1.
S. Lai, et al., "Luminescent Cyclometalated Diimine Platinum(II) Complexes: Photophysical Studies and Applications", Top Curr Chem, 2004 (month unknown), pp. 27-63, vol. 241.
H. Dias et al., "Brightly Phosphorescent Trinuclear Copper(I) Complexes of Pyrazolates: Substituent Effects on the Supramolecular Structure and Photophysics", Journal of American Chemical Society, 2005 (month unknown), pp. 7489-7501, vol. 127.
G. Ardizzoia et al., "Polynuclear pyrazolato complexes. Synthesis, chemical reactivity and crystal structures of [{Pd(dmpz)$_2$(Hdmpz)$_2$}$_2$] and [{PdAg$_2$(dmpz)$_4$}$_2$] (Hdmpz=3,5-dimethylpyrazole)", Journal of the Chemical Society, Dalton Trans. 1996 (month unknown), pp. 1351-1357.
K. Umakoshi et al., "Pyrazolato-Bridged Polynuclear Palladium and Platinum Complexes. Synthesis, Structure, and Reactivity", Inorganic Chemistry, 2003 (month unknown), pp. 3907-3916, vol. 42, No. 12.

* cited by examiner

*Primary Examiner* — Kamal A Saeed
*Assistant Examiner* — Nyeemah Grazier
(74) *Attorney, Agent, or Firm* — Buchanan Ingersoll & Rooney PC

(57) ABSTRACT

A novel luminescent metal complex comprises a composition of $[(Pt^{II})_2(Au^{I})_2(M^{I})_2(L)_8]$ where $M^I$ denotes $Ag^I$ or $Cu^I$, and L denotes a structure represented by the formula (1)

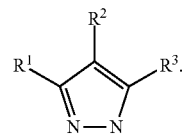

(1)

5 Claims, 5 Drawing Sheets

METAL COMPLEX, LIGHT-EMITTING DEVICE AND DISPLAY

TECHNICAL FIELD

The present invention relates to a metal complex. The present invention also relates to a light-emitting device having a light-emitting layer including the metal complex. The present invention further relates to a display having the light-emitting device.

BACKGROUND ART

Recently, organic EL devices have attracted attention as light-emitting displays alternative to liquid crystal displays. Organic EL devices according to prior arts utilize emission (fluorescence) from a singlet excited state. In such a case, a local maximum emission efficiency is 25% based on a principle of an organic EL phenomenon, and therefore the emission efficiency is extremely low.

As a method of increasing emission efficiency, phosphorescence generated from a triplet excited state has attracted particular attention recently (see Non-Patent Document 1, for example).

In such a case, the emission efficiency may be 100% in theory.

Many $Pt^{II}$ complexes having diimine or terpyridine and their derivatives exhibit emission which are assigned to MLCT (abbreviation of metal-to-ligand charge transfer; charge transfer from a metal ion to a ligand) or MMLCT (abbreviation of metal-metal-to-ligand charge transfer; charge transfer from a dσ* orbital formed by metal-metal interaction to a ligand), and photophysical properties of these compounds have attracted much interest (See Non-Patent Document 2, for example).

Polynuclear $Cu^{I}$ and $Au^{I}$ complexes of pyrazole and its derivatives are also known to exhibit emission (see Non-Patent Document 3, for example).

Accordingly, when a molecule is synthesized with $Pt^{II}$ ions and $Cu^{I}$ ions, $Ag^{I}$ ions or $Au^{I}$ ions and these metal ions are bridged by pyrazole or its derivatives, it is promising to produce a new molecule having emission properties by a synergetic effect of different metal ions.

In development of a novel metal complex based on this idea, a mixed metal complex $[Pd_2Ag_4(\mu\text{-dmpz})_8]$ having two $Pd^{II}$ ions and four $Ag^{I}$ ions bridged by 3,5-dimethylpyrazolate (denoted as dmpz, which is a monovalent anion in which a proton is dissociated from 3,5-dimethylpyrazole (dmpzH)) is known (see Non-Patent Document 4); however, emission properties of this compound have never been reported.

The present inventors also have already synthesized a mixed metal complex $[Pt_2Ag_4(\mu\text{-pz})_8]$ having $Pt^{II}$ ions and $Ag^{I}$ ions bridged by pyrazolate by using pyrazole (denoted as pz, which is a monovalent anion in which a proton is dissociated from pyrazole (pzH)) without substituent groups (see Non-Patent Document 5); however, this compound does not show emission.

Furthermore, in development of displays for commercialization, there is an increasing demand for a novel metal complex used as a dopant having improved thermal stability, volatility, film-forming properties during deposition, solubility in various solvents, emission intensity, color purity, and stability when applying a potential.

[Non-Patent Document 1] M. A. Baldo, S. Lamansky, P. E. Burrows, M. E. Thompson, S. R. Forrest, Appl. Phys. Lett., 1999, 75, 4-6.

[Non-Patent Document 2] S.-W. Lai, C.-M. Che, Topics in Current Chemistry, 2004, 241(Transition Metal and Rare Earth Compounds III), 27-63.

[Non-Patent Document 3] H. V. R. Dias, H. V. K. Diyabalanage, M. G. Eldabaja, O. Elbjeirami, M. A. Rawashdeh-Omary, M. A. Omary, J. Am. Chem. Soc., 2005, 127, 7489-7501.

[Non-Patent Document 4] G. A. Ardizzoia, G. La Monica, S. Cenini, M. Moret, N. Masciocchi, J. Chem. Soc., Dalton Trans. 1996, 1351-1357.

[Non-Patent Document 5] K. Umakoshi, Y. Yamauchi, K. Nakamiya, T. Kojima, M. Yamasaki, H. Kawano, M. Onishi, Inorg. Chem. 2003, 42, 3907-3916.

DISCLOSURE OF THE INVENTION

In view of the aforesaid problems, an object of the present invention is to provide a novel luminescent metal complex.

Another object of the present invention is to provide a novel light-emitting device having a light-emitting layer including the metal complex.

Still another object of the present invention is to provide a novel display having the light-emitting device.

In order to solve aforesaid problems and achieve the objects of the present invention, a metal complex according to an aspect of the present invention comprises the following composition:

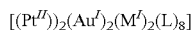

where $M^{I}$ denotes $Ag^{I}$ or $Cu^{I}$, or a combination of both, and L denotes each or a combination of any of structures represented by the formula (1). Herein L denotes a monovalent anion in which a proton is dissociated from pyrazole and its derivatives.

[formula 1]

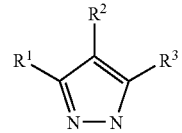

(1)

where $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.)

It is preferred that at least one of $R^1$, $R^2$ and $R^3$ in Formula (1) is not a hydrogen atom.

A light-emitting device according to another aspect of the present invention has a light-emitting layer containing the aforesaid metal complex of the present invention.

A display according to further another aspect of the present invention has the aforesaid light-emitting device of the present invention.

The present invention has the following advantages.

With the metal complex of the present invention, it is possible to provide a metal complex having excellent emission properties.

With the light-emitting device of the present invention, it is possible to provide a light-emitting device having improved emission properties by containing the metal complex of the present invention in the light-emitting layer.

With the light-emitting apparatus of the present invention, it is possible to provide a reliable light-emitting apparatus capable of displaying a high-quality image by including the aforesaid light-emitting device in the light-emitting apparatus.

BEST MODES FOR CARRYING OUT THE INVENTION

Figure 1:
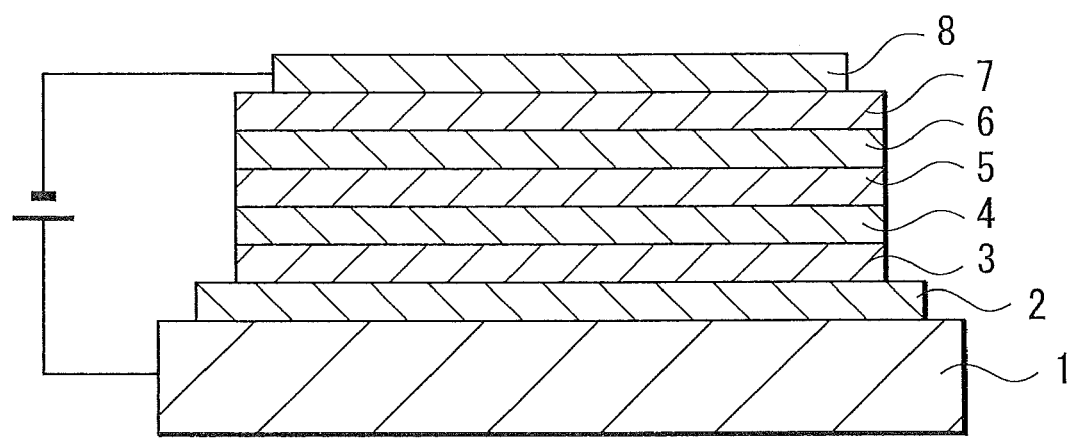
FIG. 1 is a cross-sectional view showing an example of a light-emitting device of the present invention.

A best mode for carrying out the present invention will be described below.

A metal complex of the present invention includes a composition represented by the following formula:

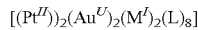

$$[(Pt^{II})_2(Au^{U})_2(M^{I})_2(L)_8]$$

where $M^I$ denotes $Ag^I$ or $Cu^I$, or a combination of both, and L denotes each or a combination of any of structures represented by the formula (1).

In the formulas, $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

More preferably, at least one of $R^1$, $R^2$ and $R^3$ in the formula (1) is not a hydrogen atom, that is, at least one of $R^1$, $R^2$ and $R^3$ is a substituent group.

In the next part, the synthesis of the metal complex of the present invention will be described. In the following, dmpzH denotes 3,5-dimethylpyrazole, and dmpz denotes a monovalent anion in which a proton is dissociated from 3,5-dimethylpyrazole.

First, the synthetic method of $[Pt_2Au_2Ag_2(\mu\text{-dmpz})_8]$ will be described as an example of the metal complex of the present invention. In the metal complex of this example, M is Ag.

This complex $[Pt_2Au_2Ag_2(\mu\text{-dmpz})_8]$ may be synthesized by the following procedure, for example.

First, $[Pt(dmpzH)_4]Cl_2$ is synthesized by reacting $[PtCl_2(C_2H_5CN)_2]$ with dmpzH.

Next, the metal complex $[Pt_2Au_2H_2(\mu\text{-dmpz})_8]$ is synthesized by reacting $[Pt(dmpzH)_4]Cl_2$ with $[AuCl(tht)]$ (tht=tetrahydrothiophene) in the presence of triethylamine in acetonitrile, and further adding $[Pt(dmpzH)_4]Cl_2$ to the reaction solution to complete the reaction.

Further, $[Pt_2Au_2Ag_2(\mu\text{-dmpz})_8]$ is obtained by reacting the metal complex $[Pt_2Au_2H_2(\mu\text{-dmpz})_8]$ with $AgBF_4$ in the presence of triethylamine in acetonitrile.

The synthetic method of $[Pt(dmpzH)_4]Cl_2$ is not limited to the aforementioned method. Alternatively, there are two other synthetic methods as follows.

One synthetic method is: suspending $[PtCl_2(C_2H_5CN)_2]$ in water, methanol or ethanol, adding an excess amount of dmpzH to the suspension, and refluxing the mixture for one hour. The solution is allowed to cool and then concentrated under reduced pressure, and acetone or diethyl ether is added to the residue to precipitate $[Pt(dmpzH)_4]Cl_2$. The precipitated $[Pt(dmpzH)_4]Cl_2$ is collected, washed with diethyl ether, and then dried under reduced pressure.

The other synthetic method is: dissolving $K_2[PtCl_4]$ in acid water, adding 4 equivalents of dmpzH, and refluxing the solution for six hours. The solution is allowed to cool and then concentrated under reduced pressure, and acetone is added to the residue to precipitate $[Pt(dmpzH)_4]Cl_2$. The precipitated $[Pt(dmpzH)_4]Cl_2$ is collected, washed with diethyl ether, and then dried under reduced pressure.

The synthetic method of $[Pt_2Au_2H_2(\mu\text{-dmpz})_8]$ is not limited to the aforementioned methods. Alternatively, there is another synthetic method described as follows.

$[Pt(dmpzH)_4]Cl_2$ is reacted with $[AuCl(tht)]$ (tht=tetrahydrothiophene) in the presence of triethylamine in acetonitrile to isolate $[PtAu_4(\mu\text{-dmpz})_4Cl_2(tht)_2]$. Further, $[Pt_2Au_2H_2(\mu\text{-dmpz})_8]$ is obtained by reacting $[PtAu_4(\mu\text{-dmpz})_4Cl_2(tht)_2]$ with $[Pt(dmpzH)_4]Cl_2$ triethylamine in acetonitrile.

Next, the synthetic method of $[Pt_2Au_2Cu_2(\mu\text{-dmpz})_8]$ will be described as an example of the metal complex of the present invention. In the metal complex of this example, M is Cu.

This complex $[Pt_2Au_2Cu_2(\mu\text{-dmpz})_8]$ may be synthesized by the following procedure, for example.

$[Pt_2Au_2Cu_2(\mu\text{-dmpz})_8]$ is synthesized by reacting the metal complex $[Pt_2Au_2H_2(\mu\text{-dmpz})_8]$, which is synthesized using the aforementioned method, with $[Cu(CH_3CN)_4] BF_4$.

Note that, the synthetic method of $[Pt_2Au_2Cu_2(\mu\text{-dmpz})_8]$ is not limited to the aforementioned methods.

In the next part, the use of the metal complex of the present invention will be described below. The metal complex can be used as a luminescent agent contained in a light-emitting layer of a light-emitting device such as an organic EL device.

However, the metal complex may not be only used as a luminescent agent. The metal complex can also be used as a sensor for organic molecules or gas molecules, an antitumor agent, or a paint that is usually colorless and transparent but emits light only when exposed to UV radiation, for example.

Next, a light-emitting device whose light-emitting layer includes such a metal complex will be described below.

FIG. 1 is a cross-sectional view showing an example of a light-emitting device of the present invention.

A substrate 1 is formed of a transparent material such as glass. An anode 2 is formed on the substrate 1. A hole injection layer 3, a hole transport layer 4, a light-emitting layer 5, an electron transport layer 6 and an electron injection layer 7 are formed on the anode 2. A cathode 8 is formed on the electron injection layer 7.

The light-emitting device of the present invention is not limited to the aforementioned five-layer light-emitting device.

Alternatively, the light-emitting device may be a four-layer light-emitting device in which the electron transport layer is omitted from the five-layer light-emitting device. The light-emitting device may also be a three-layer light-emitting device in which the hole injection layer and the electron injection layer are omitted from the five-layer light-emitting device. The light-emitting device may also be a two-layer light-emitting device having one layer used as both a light-emitting layer and an electron transport layer of the three-layer light-emitting device. The light-emitting device may also be a single-layer light-emitting device having only a light-emitting layer formed between an anode and a cathode.

The light-emitting device in which the aforementioned metal complex may be advantageously used is essentially a light-emitting device including a metal complex having light-emitting ability, and is usually mainly used as a stacked light-emitting device including an anode of applying positive voltage, a cathode of applying negative voltage, a hole injection/transport layer of injecting and transporting holes from the anode, an electron injection/transport layer of injecting and transporting electrons from the cathode, and a light-emitting layer of recombining the holes with the electrons to output light.

The aforementioned metal complex has significant light-emitting ability and is therefore extremely useful as a host luminescent agent in the light-emitting device.

Furthermore, when a slight amount of the aforementioned metal complex is doped to a hole injection/transport layer material, an electron injection/transport layer material, or another host luminescent agent including a metal complex having 8-quinolinol as a ligand such as tris(8-hydroxyquinolinato)aluminum, the aforementioned metal complex functions as a guest luminescent agent to improve their emission efficiency and emission spectra.

Therefore, in a light-emitting device including one or a plurality of such materials as essential elements, the aforementioned metal complex may be extremely advantageously used alone or in combination with other luminescent agents such as dicyanomethylene (DCM), coumarin, perylene or rubrene or a hole injection/transport layer material and/or an electron injection/transport layer material, for example.

In a stacked light-emitting device, when luminescent agents also have hole injection/transport ability or electron injection/transport ability, a hole injection/transport layer or an electron injection/transport layer may be omitted, or when one of a hole injection/transport layer and an electron injection/transport layer functions as the other, the hole injection/transport layer or the electron injection/transport layer may be omitted, respectively.

The metal complex of the present invention may be used for both a single-layer light-emitting device and a stacked light-emitting device.

An operation of a light-emitting device essentially includes a process of injecting electrons and holes from electrodes, a process of transferring the electrons and the holes in a solid, a process of recombining the electrons with the holes to produce a triplet exciton, and a process of allowing the exciton to emit light. These processes are essentially not different between a single-layer light-emitting device and a stacked light-emitting device.

However, a stacked light-emitting device may generally provide desired performance more easily as compared with a single-layer light-emitting device. While in the single-layer light-emitting device, characteristics of the four processes may be improved only by changing the molecular structure of a luminescent agent, in the stacked light-emitting device, functions required for each process may be shared by a plurality of materials and each material may be independently optimized. Thus, desired performance may be more easily achieved in a case where the metal complex is formed in the stacked light-emitting device than in a case where the metal complex is formed in the single-layer light-emitting device.

The aforementioned light-emitting device may be used in a display. Specifically, a display including the light-emitting device as a component may include the aforementioned metal complex in a light-emitting layer of the light-emitting device.

The present invention is not limited to the aforementioned best mode for carrying out the present invention. Obviously, various other embodiments can be provided without departing from the gist of the present invention.

EXAMPLES

Examples of the present invention will be specifically described below. However, it should be noted that the present invention is not limited to these examples.

Example 1

A metal complex $[Pt_2Au_2H_2(\mu\text{-dmpz})_8]$ was synthesized as a precursor, and $[Pt_2Au_2Ag_2(\mu\text{-dmpz})_8]$, which is an example of the metal complex of the present invention, was synthesized by using the precursor.

Details of the synthetic method of the metal complex will be described below.

First, $[Pt(dmpzH)_4]Cl_2$ was synthesized.

Specifically, a solution of dmpzH (1155 mg, 12.0 mmol) in toluene (40 ml) was added to a suspension of $[PtCl_2(C_2H_5CN)_2]$ (1130 mg, 3.0 mmol) in toluene (20 ml), and the mixture was refluxed for three hours under an Ar atmosphere. The resultant white precipitate was collected, sequentially washed with toluene, hexane and diethyl ether, and then dried under reduced pressure. The yield was 1905 mg (97.5%).

The synthetic method of $[Pt(dmpzH)_4]Cl_2$ is shown in chemical reaction formula 1.

[Chemical reaction formula 1]

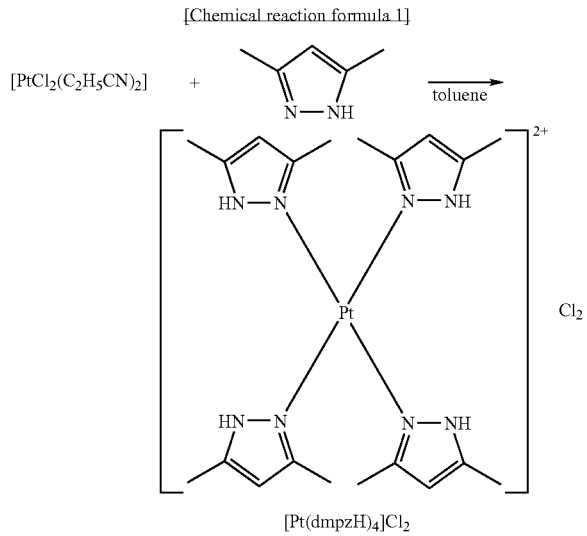

The product was identified by IR and $^1$H NMR spectra.
The infrared frequencies are as follows.
IR (KBr): 3121 (m), 3068 (s), 2927 (s), 2849 (s), 2765 (s), 1580 (s), 1420 (m), 1297 (m), 195 (w), 1150 (w), 1075 (w), 806 (m)
The $^1$H NMR data are summarized in Table 1.

TABLE 1

$^1$H NMR of $[Pt(dmpzH)_4]Cl_2$ (in $CD_3OD$, 300 MHz)

| δ (ppm) | Shape (J/Hz) | Int. | Assign. |
|---|---|---|---|
| 6.12 | s | 1 | H4 of dmpzH |
| 2.29 | s | 3 | 5-$CH_3$ of dmpzH |
| 1.94 | s | 3 | 3-$CH_3$ of dmpzH |

Next, the precursor metal complex $[Pt_2Au_2H_2(\mu\text{-dmpz})_8]$ was synthesized from $[Pt(dmpzH)_4]Cl_2$.

Specifically, under an Ar atmosphere, a solution of AuCl(tht) (123 mg, 0.4 mmol) in $CH_3CN$ (20 ml) and $Et_3N$ (73 μl, 0.05 mmol) were added into a solution of $[Pt(dmpzH)_4]Cl_2$ (65 mg, 0.1 mmol) in $CH_3CN$ (20 ml), and the resultant solution was stirred for two hours. Thereafter, a solution of $[Pt(dmpzH)_4]Cl_2$ (33 mg, 0.05 mmol) in $CH_3CN$ (10 ml) and $Et_3N$ (55 μl, 0.038 mmol) were added to the solution with stirring, and the resultant solution was further stirred for two hours. The solution was filtered and then concentrated under air, and the precipitated solid was collected, washed with acetonitrile, and then dried under reduced pressure. The yield was 83 mg (57%). The complex was recrystallized from chloroform/acetonitrile.

The synthetic method of the metal complex $[Pt_2Au_2H_2(\mu\text{-}dmpz)_8]$ is shown in chemical reaction formula 2.

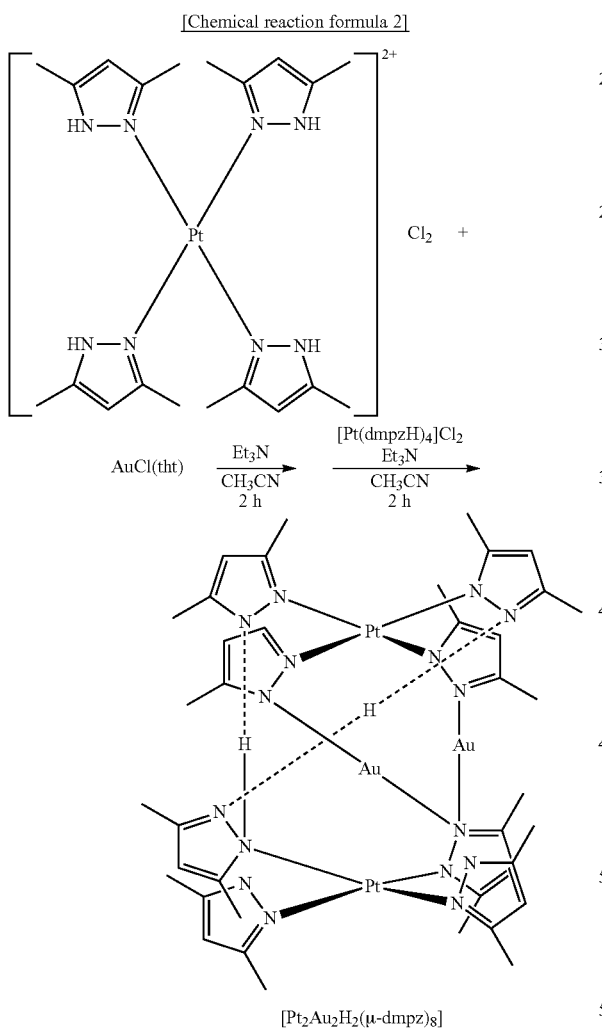

[Chemical reaction formula 2]

The obtained compound exhibits yellow luminescence in the solid state upon exposure to UV radiation, and its emission spectrum has the local maximum at 544 nm. The emission quantum yield of the compound was 0.08 in the solid state. However, the compound only showed weak emission in dichloromethane.

With regard to solubility in a solvent, the compound is soluble in chloroform and methylene chloride, slightly soluble in ether and acetone, and hardly-soluble in acetonitrile, methanol and toluene.

The product was identified by elemental analysis, and IR and $^1H$ NMR spectra.

The result of the elemental analysis of the product is shown in Table 2.

TABLE 2

Elemental Analysis of $[Pt_2Au_2H_2 (\mu\text{-}dmpz)_8]$

|  | Calc. | Found | Δ |
|---|---|---|---|
| C (%) | 31.05 | 31.46 | +0.41 |
| H (%) | 3.78 | 3.61 | −0.17 |
| N (%) | 14.49 | 14.58 | +0.09 |

The infrared frequencies are as follows.

IR (KBr): 3113 (w), 2957 (w), 2919 (s), 2853 (w), 1863 (br), 1572 (s), 1533 (s), 1417 (s), 1367 (m), 1170 (w), 1147 (w), 1036 (w), 981 (w), 765 (s), 652 (w), 592 (w), 487 (w), 375 (w), 325 (w)

The $^1H$ NMR data are summarized in Table 3.

TABLE 3

$^1H$ NMR data of $[Pt_2Au_2H_2(\mu\text{-}dmpz)_8]$ (CDCl$_3$, TMS, 300 MHz)

| δ (ppm) | Shape(J/Hz) | Int. | Assign. |
|---|---|---|---|
| 17.78 | s | 1 | NH |
| 5.74 | s | 1 | H4 of dmpz |
| 5.68 | s | 1 | H4 of dmpz |
| 5.58 | s | 1 | H4 of dmpz |
| 5.45 | s | 1 | H4 of dmpz |
| 2.08 | s | 3 | CH$_3$ of dmpz |
| 1.90 | s | 3 | CH$_3$ of dmpz |
| 1.89 | s | 3 | CH$_3$ of dmpz |
| 1.86 | s | 3 | CH$_3$ of dmpz |
| 1.85 | s | 3 | CH$_3$ of dmpz |
| 1.82 | s | 3 | CH$_3$ of dmpz |
| 1.64 | s | 3 | CH$_3$ of dmpz |
| 1.56 | s | 3 | CH$_3$ of dmpz |

Next, the metal complex $[Pt_2Au_2Ag_2(\mu\text{-}dmpz)_8]$ was synthesized from the precursor metal complex $[Pt_2Au_2H_2(\mu\text{-}dmpz)_8]$.

Specifically, a solution of $[Pt_2Au_2H_2(\mu\text{-}dmpz)_8]$ (50 mg, 0.033 mmol) in $CH_3CN$ (30 ml) and a solution of $AgBF_4$ (13 mg, 0.067 mmol) in $CH_3CN$ (10 ml) were mixed with each other, a solution of $Et_3N$ (9.2 μl, 0.066 mmol) in $CH_3CN$ (10 ml) was added, and the resultant solution was stirred for twelve hours. Thereafter, the precipitated solid was filtered off and dried under reduced pressure. The yield was 36 mg (61%). The complex was recrystallized from chloroform/acetonitrile.

The synthetic method of the metal complex $[Pt_2Au_2Ag_2(\mu\text{-}dmpz)_8]$ is shown in chemical reaction formula 3.

[Chemical reaction formula 3]

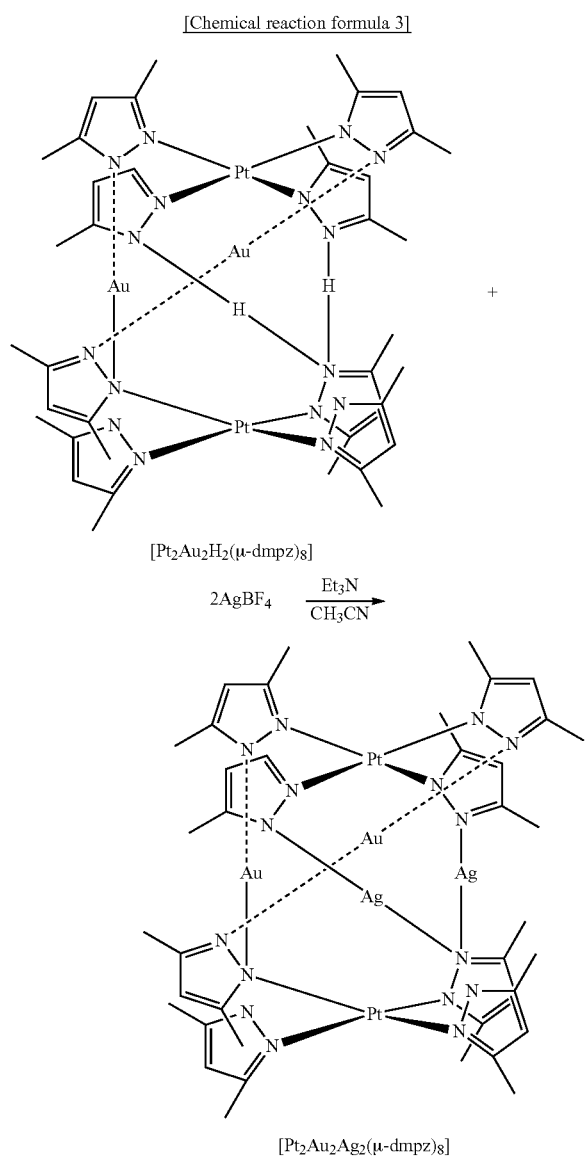

[Pt$_2$Au$_2$H$_2$($\mu$-dmpz)$_8$]

2AgBF$_4$ $\xrightarrow[\text{CH}_3\text{CN}]{\text{Et}_3\text{N}}$

[Pt$_2$Au$_2$Ag$_2$($\mu$-dmpz)$_8$]

The obtained compound exhibits sky-blue luminescence in the solid state upon exposure to UV radiation.

With regard to solubility in a solvent, the compound is soluble in chloroform and methylene chloride, slightly soluble in ether and acetone, and hardly-soluble in acetonitrile, methanol and toluene.

The product was identified by elemental analysis, and IR and $^1$H NMR spectra.

The result of the elemental analysis of the product is shown in Table 4.

TABLE 4

|       | Calc. | Found | Δ     |
|-------|-------|-------|-------|
| C (%) | 27.28 | 27.19 | −0.09 |
| H (%) | 3.21  | 2.89  | −0.32 |
| N (%) | 12.73 | 12.74 | +0.01 |

The infrared frequencies are as follows.

IR (KBr): 3117 (w), 2971 (w), 2917 (s), 2856 (w), 1531 (s), 1421 (s), 1354 (m), 1161 (w), 1050 (m), 979 (w), 763 (s), 652 (w), 592 (w), 379 (w), 338 (w)

The $^1$H NMR data are summarized in Table 5.

TABLE 5

$^1$H NMR data of [Pt$_2$Au$_2$Ag$_2$($\mu$-dmpz)$_8$] (CDCl$_3$, TMS, 300 MHz)

| δ (ppm) | Shape | Int. | Assign. |
|---------|-------|------|---------|
| 5.76    | s     | 2    | H4 of dmpz |
| 5.67    | s     | 2    | H4 of dmpz |
| 1.94    | s     | 9    | CH$_3$ of dmpz |
| 1.92    | s     | 3    | CH$_3$ of dmpz |
| 1.89    | s     | 3    | CH$_3$ of dmpz |
| 1.88    | s     | 3    | CH$_3$ of dmpz |
| 1.86    | s     | 3    | CH$_3$ of dmpz |
| 1.75    | s     | 3    | CH$_3$ of dmpz |

Further, mass spectroscopy was performed by FABMS. The result is as follows.

FABMS: m/z: 1760.1 [M$^+$]

Example 2

A metal complex [Pt$_2$Au$_2$H$_2$($\mu$-dmpz)$_8$] was synthesized as a precursor, and [Pt$_2$Au$_2$Cu$_2$($\mu$-dmpz)$_8$], which is an example of the metal complex of the present invention, was synthesized by using the precursor.

Details of the synthetic method of the metal complex will be described below.

First, the precursor metal complex [Pt$_2$Au$_2$H$_2$($\mu$-dmpz)$_8$] was synthesized using the same method as described in Example 1.

Next, the metal complex [Pt$_2$Au$_2$Cu$_2$($\mu$-dmpz)$_8$] was synthesized from the precursor metal complex [Pt$_2$Au$_2$H$_2$($\mu$-dmpz)$_8$].

Specifically, under an Ar atmosphere, a solution of [Pt$_2$Au$_2$H$_2$($\mu$-dmpz)$_8$] (100 mg, 0.066 mmol) in CH$_2$Cl$_2$ (30 ml) and a solution of [Cu(CH$_3$CN)$_4$]BF$_4$ (42 mg, 0.134 mmol) in CH$_2$Cl$_2$ (10 ml) were mixed with each other, and the resultant solution was stirred for fourteen hours. The reaction solution was filtered, and the filtrate was concentrated by an evaporator. Precipitate resulted by adding a small amount of CH$_3$CN was filtered off and dried under reduced pressure. The yield was 32 mg (30%). The complex was recrystallized from chloroform/acetonitrile.

The synthetic method of the metal complex [Pt$_2$Au$_2$Cu$_2$($\mu$-dmpz)$_8$] is shown in chemical reaction formula 4.

[Chemical reaction formula 4]

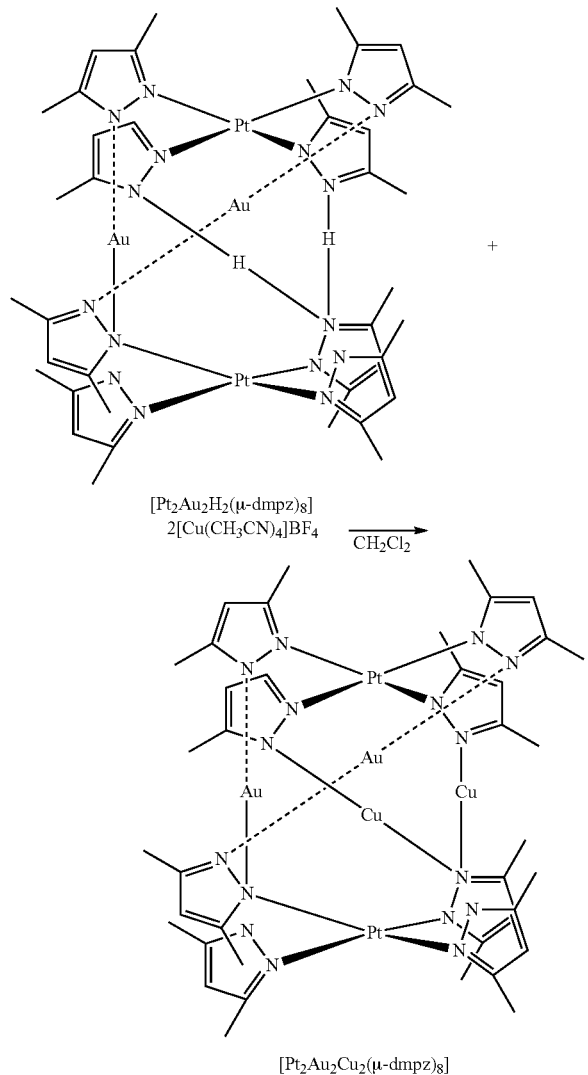

[Pt₂Au₂H₂(μ-dmpz)₈]
2[Cu(CH₃CN)₄]BF₄ →(CH₂Cl₂)

[Pt₂Au₂Cu₂(μ-dmpz)₈]

The obtained compound exhibits orange luminescence in the solid state upon exposure to UV radiation.

With regard to solubility in a solvent, the compound is soluble in chloroform and methylene chloride, slightly soluble in ether and acetone, and hardly-soluble in acetonitrile, methanol and toluene.

The product was identified by elemental analysis, and IR and $^1$H NMR spectra.

The result of the elemental analysis of the product is shown in Table 6.

TABLE 6

|  | Calc. | Found | Δ |
|---|---|---|---|
| C (%) | 28.73 | 28.77 | +0.04 |
| H (%) | 3.38 | 3.18 | −0.20 |
| N (%) | 13.40 | 13.50 | +0.10 |

The infrared frequencies are as follows.

IR (KBr): 3117 (w), 2970 (w), 2916 (s), 2856 (w), 2362 (w), 1532 (s), 1422 (s), 1359 (m), 1158 (w), 1083 (w), 1055 (w), 1035 (w), 980 (w), 760 (s), 652 (w), 592 (w), 481 (w), 350 (w)

The $^1$H NMR data are summarized in Table 7.

TABLE 7

$^1$H NMR data of [Pt₂Au₂Cu₂(μ-dmpz)₈] (CDCl₃, TMS, 300 MHz)

| δ (ppm) | Shape | Int. | Assign. |
|---|---|---|---|
| 5.76 | s | 1 | H4 of dmpz |
| 5.73 | s | 1 | H4 of dmpz |
| 5.63 | s | 1 | H4 of dmpz |
| 5.60 | s | 1 | H4 of dmpz |
| 1.98 | s | 3 | CH₃ of dmpz |
| 1.92 | s | 3 | CH₃ of dmpz |
| 1.90 | s | 3 | CH₃ of dmpz |
| 1.88 | s | 3 | CH₃ of dmpz |
| 1.85 | s | 3 | CH₃ of dmpz |
| 1.83 | s | 3 | CH₃ of dmpz |
| 1.81 | s | 3 | CH₃ of dmpz |
| 1.77 | s | 3 | CH₃ of dmpz |

Further, mass spectroscopy was performed by FABMS. The result is as follows.

FABMS: m/z: 1672.2 [M⁺]

Further, the structure and emission properties of the finally produced metal complexes in the respective examples will be described below.

The molecular structure of the metal complex [Pt₂Au₂H₂(μ-dmpz)₈] used as precursor was determined by single crystal X-ray structural analysis, and the crystallographic data are shown in Table 8.

TABLE 8

Crystallographic Data of [Pt₂Au₂H₂(μ-dmpz)₈]

| | [Pt₂Au₂H₂(μ-dmpz)₈] |
|---|---|
| empirical formula | C₄₀H₅₈Au₂N₁₆Pt₂ |
| fw | 1547.12 |
| T, K | 296 |
| λ, Å | 0.71070 |
| cryst syst | monoclinic |
| space group | C2/c (# 15) |
| a, Å | 39.572(2) |
| b, Å | 11.7455(5) |
| c, Å | 21.379(1) |
| β, deg | 100.2401(5) |
| V, Å³ | 9778.7(8) |
| Z | 8 |
| $\rho_{calcd}$, g cm⁻³ | 2.102 |
| μ(Mo Kα), mm⁻¹ | 11.731 |
| no. of unique rflns | 11112 ($R_{int}$ = 0.031) |
| data/restraints/params | 11111/0/549 |
| final R indices [I > 2σ(I)] | R1 = 0.040 |
| R indices (all data) | R = 0.058, $R_w$ = 0.108 |
| GOF | 1.07 |

Here, the items in the table denote, from top to bottom, composition, formula weight, measured temperature, measured wavelength, crystal system, space group, lattice constants (a, b, c, β), unit cell volume, Z value, density, linear absorption coefficient, number of unique reflections, numbers of data and parameters, final R index, R index when total reflection is used, and GOF value, respectively.

Figure 2:
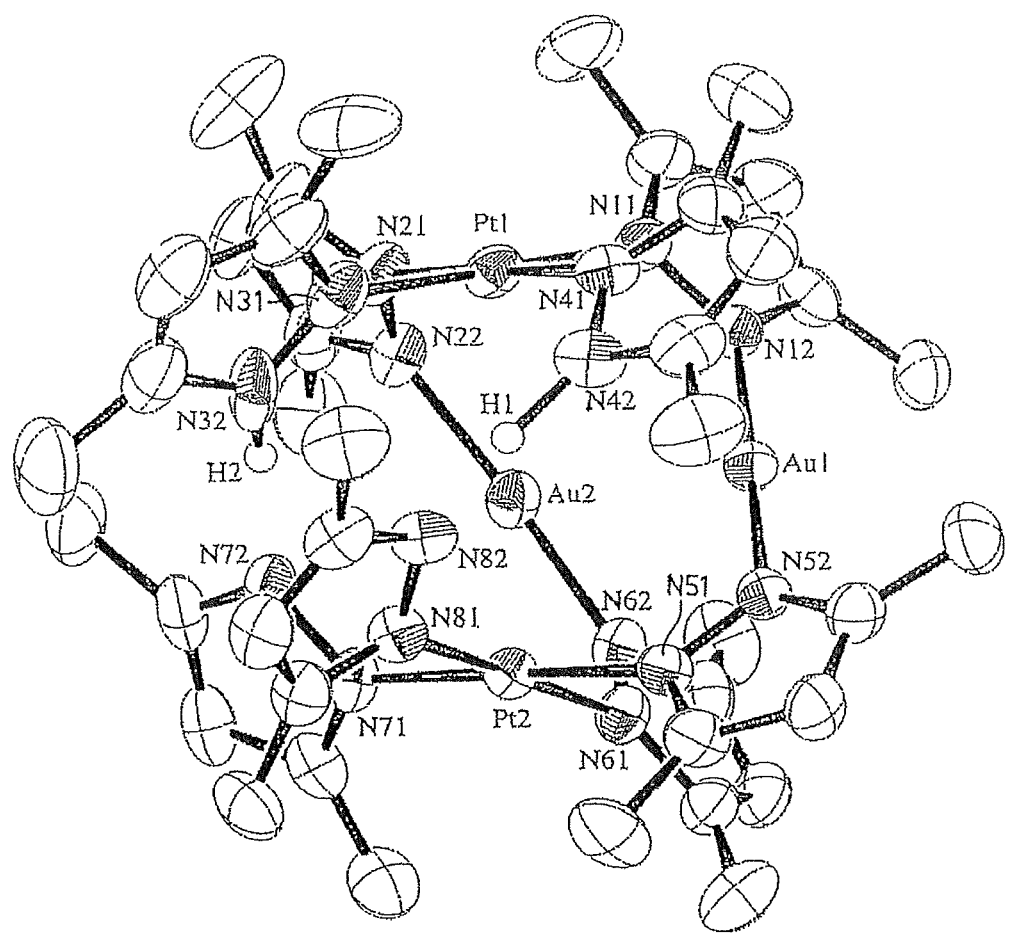
FIG. 2 is an ORTEP diagram showing a molecular structure of $[Pt_2Au_2H_2(\mu\text{-dmpz})_8]$.

The molecular structure of the metal complex [Pt₂Au₂H₂(μ-dmpz)₈] is shown in the ORTEP diagram of FIG. 2.

As shown in FIG. 2, the molecular structure of the metal complex [Pt₂Au₂H₂(μ-dmpz)₈] consists of two Pt$^{II}$ ions, two Au$^{I}$ ions, six dmpz ligands and two dmpzH ligands, and is equivalent to a structure formed by replacing two adjacent M atoms of the molecular structure of [Pt₂M₄(μ-dmpz)₈] (M=Ag,Cu) with hydrogen atoms. Since the hydrogen atoms, which replace M atoms, each form an intramolecular hydrogen bond between two dmpz ligands coordinating to the respective Pt atoms, two Pt coordination planes are not parallel to each other. The Pt1 . . . Pt2 distance is 4.4640(4)Å, which is 0.69 Å shorter than the Pt . . . Pt distance of [Pt$_2$Ag$_4$(μ-dmpz)$_8$] (5.1578(8)Å) and 0.19 Å shorter than the Pt . . . Pt distance of [Pt$_2$Cu$_4$(μ-dmpz)$_8$] (4.6567(5)Å).

The molecular structures of the finally produced metal complexes [Pt$_2$Au$_2$Ag$_2$(μ-dmpz)$_8$] and [Pt$_2$Au$_2$Cu$_2$(μ-dmpz)$_8$] in the respective examples were also determined by single crystal X-ray structural analysis. The crystallographic data of [Pt$_2$Au$_2$Ag$_2$(μ-dmpz)$_8$] and [Pt$_2$Au$_2$Cu$_2$(μ-dmpz)$_8$] are shown in Table 9.

TABLE 9

Crystallographic Data of [Pt$_2$Au$_2$Ag$_2$(μ-dmpz)$_8$] and [Pt$_2$Au$_2$Cu$_2$(μ-dmpz)$_8$]

| | [Pt$_2$Au$_2$Ag$_2$(μ-dmpz)$_8$] | [Pt$_2$Au$_2$Cu$_2$(μ-dmpz)$_8$] |
|---|---|---|
| empirical formula | C$_{40}$H$_{56}$Au$_2$Ag$_2$N$_{16}$Pt$_2$ | C$_{40}$H$_{56}$Au$_2$Cu$_2$N$_{16}$Pt$_2$ |
| fw | 1760.84 | 1672.19 |
| T, K | 296 | 296 |
| λ, Å | 0.71070 | 0.71070 |
| cryst syst | monoclinic | monoclinic |
| space group | C2/c (#15) | C2/c (#15) |
| a, Å | 20.672(1) | 20.076(2) |
| b, Å | 12.9501(7) | 13.1601(9) |
| c, Å | 19.524(2) | 19.634(1) |
| α, deg | 90 | 90 |
| β, deg | 105.113(1) | 105.9426(7) |
| γ, deg | 90 | 90 |
| V, Å$^3$ | 5046.1(6) | 4987.9(6) |
| Z | 4 | 4 |
| ρ$_{calcd}$, Mg m$^{-3}$ | 2.318 | 2.227 |
| μ(Mo Kα), cm$^{-1}$ | 121.19 | 123.30 |
| no. of unique rflns | 5540 (R$_{int}$ = 0.034) | 5629 (R$_{int}$ = 0.037) |
| data/restraints/params | 5540/0/280 | 5629/0/280 |
| final R indices [I > 2σ(I)] | R1 = 0.030 | R1 = 0.052 |
| R indices (all data) | R = 0.049, R$_w$ = 0.080 | R = 0.089, R$_w$ = 0.148 |
| GOF | 0.87 | 1.10 |

Figure 3:
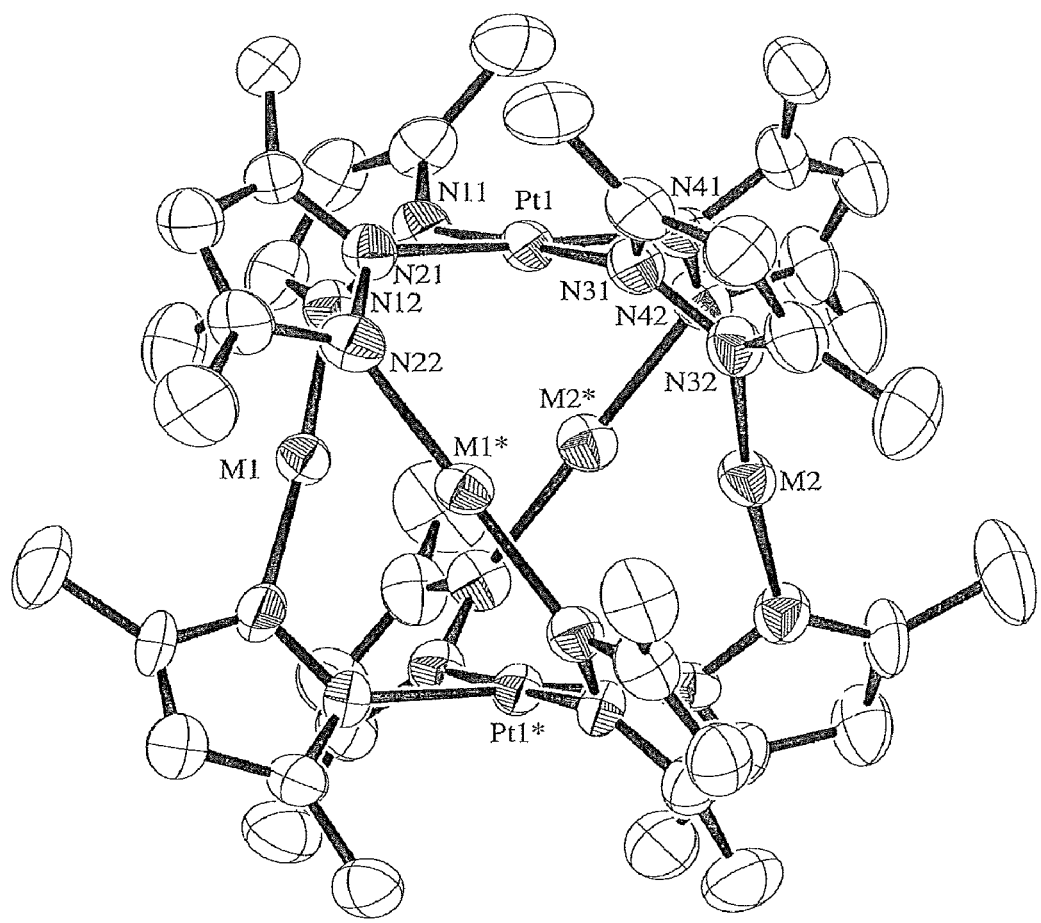
FIG. 3 is an ORTEP diagram showing a molecular structure of $[Pt_2Au_2Ag_2(\mu\text{-dmpz})_8]$.

The molecular structure of the metal complex [Pt$_2$Au$_2$Ag$_2$(μ-dmpz)$_8$] is shown in the ORTEP diagram of FIG. 3.

As shown in FIG. 3, the metal complex [Pt$_2$Au$_2$Ag$_2$(μ-dmpz)$_8$] has a structure obtained by replacing the two bridging H$^+$ ions of [Pt$_2$Au$_2$H$_2$(μ-dmpz)$_8$] shown in FIG. 2 with Ag$^I$ ions.

This [Pt$_2$Au$_2$Ag$_2$(μ-dmpz)$_8$] has a pseudo 4-fold axis passing through the two Pt atoms and a crystallographically imposed 2-fold axis perpendicular to the 4-fold rotation axis. The 2-fold axis passes through the midpoint of M1 . . . M1* and the midpoint of M2 . . . M2*. The Au atoms and Ag atoms are disordered in the crystal. The occupancies of Au atom and Ag atom for M1 site are 0.55 and 0.45 respectively, and those of Au atom and Ag atom for M2 site are 0.45 and 0.55 respectively.

Selected bond distances of this [Pt$_2$Au$_2$Ag$_2$(μ-dmpz)$_8$] are shown in Table 10.

TABLE 10

Selected Bond Distances (Å)

| | | |
|---|---|---|
| Pt1-Pt1*: 5.1038(6) | M1-Pt1: 3.5400(5) | M2-Pt1: 3.5202(5) |
| M1*-Pt1: 3.4830(4) | M2*-Pt1: 3.5229(5) | M1-M1*: 3.4011(7) |
| M2-M2*: 3.3441(8) | M1-M2: 4.8387(5) | M1-M2*: 3.4702(6) |

As shown in Table 10, in [Pt$_2$Au$_2$Ag$_2$(μ-dmpz)$_8$], the Pt . . . Pt distance is 5.1038(6)Å, and the Pt . . . M distances are in a range of 3.4830(4)Å-3.5400(5)Å. Further, the adjacent M . . . M distances are in a range of 3.3441(8)Å-3.4702(6)Å, and the diagonal M . . . M distance is 4.8387(5)Å.

Figure 4:
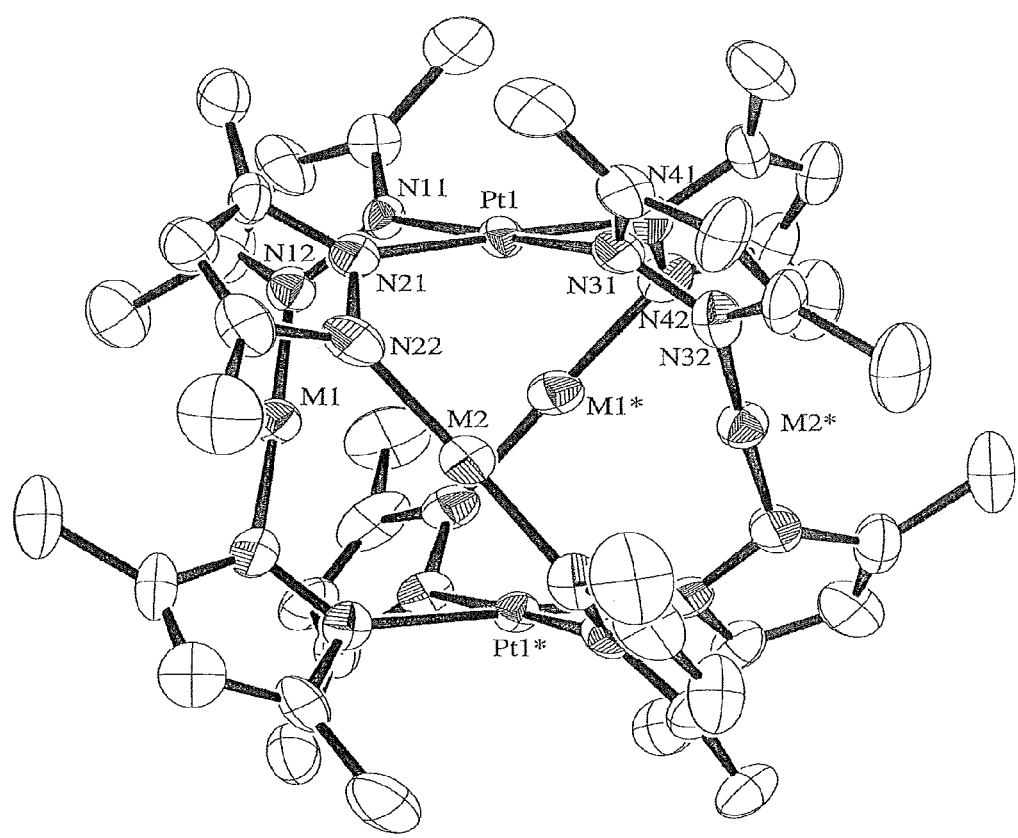
FIG. 4 is an ORTEP diagram showing a molecular structure of $[Pt_2Au_2Cu_2(\mu\text{-dmpz})_8]$.

The molecular structure of the metal complex [Pt$_2$Au$_2$Cu$_2$(μ-dmpz)$_8$] is shown in the ORTEP diagram of FIG. 4.

As shown in FIG. 4, the metal complex [Pt$_2$Au$_2$Cu$_2$(μ-dmpz)$_8$] has a structure obtained by replacing the two bridging H$^+$ ions of [Pt$_2$Au$_2$H$_2$(μ-dmpz)$_8$] shown in FIG. 2 with Cu$^I$ ions.

This [Pt$_2$Au$_2$Cu$_2$(μ-dmpz)$_8$] has a pseudo 4-fold axis passing through the two Pt atoms and a crystallographically imposed 2-fold axis perpendicular to the 4-fold rotation axis. The 2-fold axis passes through the midpoint of M1 . . . M1* and the midpoint of M2 . . . M2*. The Au atoms and Cu atoms are disordered in the crystal. The occupancies of Au atom and Cu atom are 0.5, respectively, both for M1 and M2 sites.

Selected bond distances of this [Pt$_2$Au$_2$Cu$_2$(μ-dmpz)$_8$] are shown in Table 11.

TABLE 11

Selected Bond Distances (Å)

| | | |
|---|---|---|
| Pt1 . . . Pt1*: 4.7748(9) | M1 . . . Pt1: 3.4583(8) | M2 . . . Pt1: 3.4945(9) |
| M1* . . . Pt1: 3.502(1) | M2* . . . Pt1: 3.479(1) | M1 . . . M1*: 3.557(2) |
| M2 . . . M2*: 3.499(2) | M1 . . . M2: 3.645(1) | M1 . . . M2*: 5.073(1) |

As shown in Table 11, in [Pt$_2$Au$_2$Cu$_2$(μ-dmpz)$_8$], the Pt . . . Pt distance is 4.7748(9)Å, and the Pt . . . M distances are in a range of 3.4583(8)Å-3.502(1)Å. Further, the adjacent M . . . M distances are in a range of 3.499(2)Å-3.645(1)Å, and the diagonal M . . . M distance is 5.073(1)Å.

Next, photophysical properties of each of the metal complexes will be described below.

[Pt$_2$Au$_2$Ag$_2$(μ-dmpz)$_8$] exhibits sky-blue luminescence in the solid state with an emission maximum wavelength at 495 nm, and exhibits green luminescence in dichloromethane with an emission maximum wavelength at 529 nm. The emission quantum yields were Φ=0.28 in the solid state and Φ=0.032 in dichloromethane, respectively.

The emission maximum wavelengths of [Pt$_2$Au$_2$Ag$_2$(μ-dmpz)$_8$] in the solid state and in dichloromethane are very close to those of [Pt$_2$Ag$_4$(μ-dmpz)$_8$], respectively. However, since the half width of the emission spectrum of [Pt$_2$Au$_2$Ag$_2$(μ-dmpz)$_8$] is wider than that of [Pt$_2$Ag$_4$(μ-dmpz)$_8$], the color of the luminescence of [Pt$_2$Au$_2$Ag$_2$(μ-dmpz)$_8$] is slightly different from that of [Pt$_2$Ag$_4$(μ-dmpz)$_8$] in the solid state.

Emission spectra and emission decay curves in the solid state and in dichloromethane were measured respectively. The emission decay curves were analyzed by a biexponential function (I(t)=A$_1$exp(−t/τ$_1$)+A$_2$exp(−t/τ$_2$)) both in the solid state and in dichloromethane.

Figure 5A:
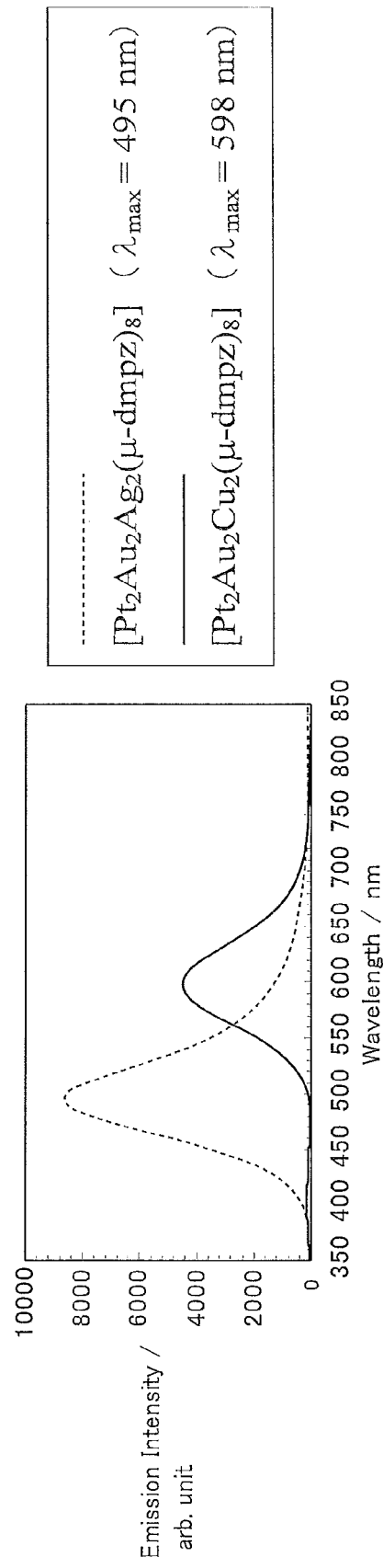
FIG. 5A shows emission spectra of $[Pt_2Au_2Ag_2(\mu\text{-dmpz})_8]$ and $[Pt_2Au_2Cu_2(\mu\text{-dmpz})_8]$ in the solid state.
Figure 5B:
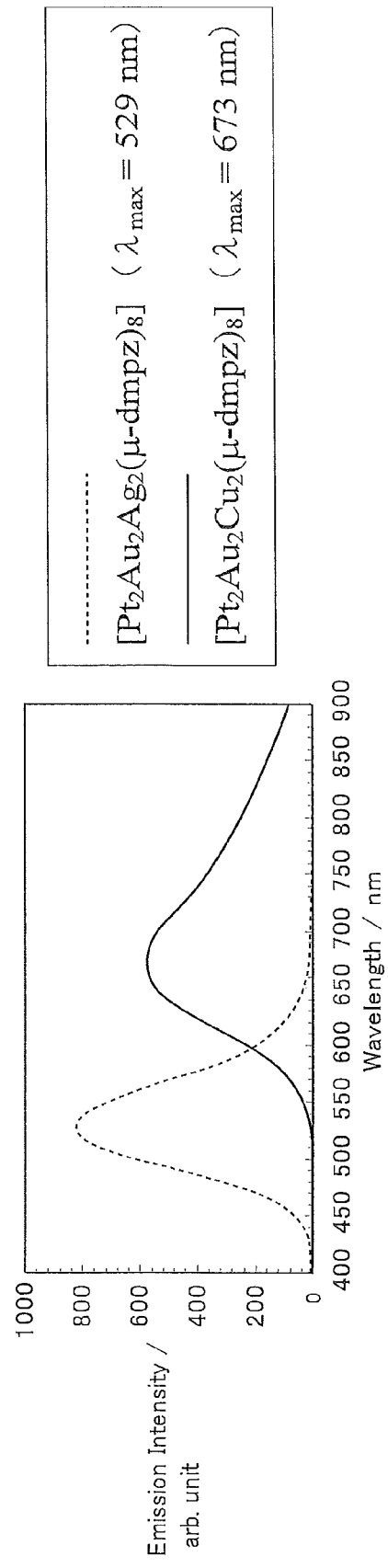
FIG. 5B shows emission spectra of $[Pt_2Au_2Ag_2(\mu\text{-dmpz})_8]$ and $[Pt_2Au_2Cu_2(\mu\text{-dmpz})_8]$ in dichloromethane.

The result of the measurement is shown in Table 12. Further, the emission spectra of [Pt$_2$Au$_2$Ag$_2$(μ-dmpz)$_8$] are shown in FIG. 5A and FIG. 5B. FIG. 5A shows the emission spectra in the solid state, and FIG. 5B shows the emission spectra in dichloromethane.

TABLE 12

Emission decay parameters of [Pt$_2$Au$_2$Ag$_2$(μ-dmpz)$_8$] and [Pt$_2$Au$_2$Cu$_2$(μ-dmpz)$_8$] in solid and in CH$_2$Cl$_2$

| | | τ$_1$/μs | A$_1$ | τ$_2$/μs | A$_2$ |
|---|---|---|---|---|---|
| [Pt$_2$Au$_2$Ag$_2$(μ-Me$_2$pz)$_8$] | solid | 3.6 | 0.58 | 8.4 | 0.42 |
| | CH$_2$Cl$_2$ | 0.43 | 0.34 | 6.2 | 0.66 |
| [Pt$_2$Au$_2$Cu$_2$(μ-Me$_2$pz)$_8$] | solid | 3.5 | 0.71 | 12.8 | 0.29 |
| | CH$_2$Cl$_2$ | 0.81 | 0.25 | 5.8 | 0.75 |

It can be known from Table 12 that, since the emission lifetime of [Pt$_2$Au$_2$Ag$_2$(μ-dmpz)$_8$] is relatively long, the emissive state for [Pt$_2$Au$_2$Ag$_2$(μ-dmpz)$_8$] might be assigned to a triplet excited state in the same manner as other similar complexes.

On the other hand, [Pt$_2$Au$_2$Cu$_2$(μ-dmpz)$_8$] exhibits orange luminescence in the solid state with an emission maximum wavelength at 598 nm, and exhibits red luminescence in dichloromethane with an emission maximum wavelength at 673 nm. The emission quantum yields were Φ=0.20 in the solid state and Φ=0.040 in dichloromethane, respectively.

Since the emission maximum wavelengths of [Pt$_2$Au$_2$Cu$_2$(μ-dmpz)$_8$] both in the solid state and in dichloromethane are largely shifted from those of [Pt$_2$Cu$_4$(μ-dmpz)$_8$] (625 nm in the solid state and 820 nm in dichloromethane), there is no reason to consider the contribution of emission by [Pt$_2$Cu$_4$(μ-dmpz)$_8$] to the emission spectra of [Pt$_2$Au$_2$Cu$_2$(μ-dmpz)$_8$].

This indicates that a crystal of [Pt$_2$Au$_2$Cu$_2$(μ-dmpz)$_8$] is not a mixture of [Pt$_2$Au$_4$(μ-dmpz)$_8$] and [Pt$_2$Cu$_4$(μ-dmpz)$_8$], but undoubtedly is a mixed metal complex whose molecule contains the same number of Au atoms and Cu atoms.

Measurements of emission spectra and emission decay curves in the solid state and in dichloromethane are respectively performed on [Pt$_2$Au$_2$Cu$_2$(μ-dmpz)$_8$]. The emission decay curves were analyzed by the biexponential function both in the solid state and in dichloromethane.

The results of the measurement are also shown in Table 12. Further, the emission spectra of [Pt$_2$Au$_2$Cu$_2$(μ-dmpz)$_8$] both in the solid state and in dichloromethane are also shown in FIG. 5A and FIG. 5B.

It can be known from Table 12 that, since the emission lifetime of [Pt$_2$Au$_2$Cu$_2$(μ-dmpz)$_8$] is relatively long, the emissive state for [Pt$_2$Au$_2$Cu$_2$(μ-dmpz)$_8$] might be assigned to a triplet excited state in the same manner as other similar metal complexes.

As described above, the metal complex of the present invention has potential for industrial applications such as light-emitting device and display.

EXPLANATION OF REFERENCE NUMERALS

1 substrate
2 anode
3 hole injection layer
4 hole transport layer
5 light-emitting layer
6 electron transport layer
7 electron injection layer
8 cathode

The invention claimed is:

1. A metal complex comprising the following composition:

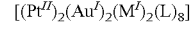

where M$^I$ denotes Ag$^I$ or Cu$^I$, and L denotes a structure represented by the formula (I),

where R$^1$, R$^2$ and R$^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

2. The metal complex according to claim 1, wherein at least one of R$^1$, R$^2$ and R$^3$ in the formula is not a hydrogen atom.

3. A light-emitting device comprising a light-emitting layer containing the metal complex according to claim 1.

4. A display comprising the light-emitting device according to claim 3.

5. A light-emitting device comprising a light-emitting layer containing the metal complex according to claim 2.

* * * * *